United States Patent
Mosnier et al.

(10) Patent No.: US 12,019,955 B2
(45) Date of Patent: *Jun. 25, 2024

(54) METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT'S VERTEBRAL COLUMN

(71) Applicant: Medicrea International, Rillieux-la-Pape (FR)

(72) Inventors: Thomas Mosnier, Rochetaillee sur Saone (FR); David N. Ryan, Collonges au Mont d'or (FR); Vincent Fiere, Lyons (FR)

(73) Assignee: MEDICREA INTERNATIONAL (FR)

( * ) Notice: Subject to any disclaimer, the term of this patent is extended or adjusted under 35 U.S.C. 154(b) by 673 days.

This patent is subject to a terminal disclaimer.

(21) Appl. No.: 17/188,261

(22) Filed: Mar. 1, 2021

(65) Prior Publication Data
US 2021/0216671 A1 Jul. 15, 2021

Related U.S. Application Data

(63) Continuation of application No. 16/389,348, filed on Apr. 19, 2019, now Pat. No. 10,970,426, which is a (Continued)

(30) Foreign Application Priority Data

Sep. 18, 2013 (FR) ...................................... 1358988

(51) Int. Cl.
*G06F 30/00* (2020.01)
*A61B 17/56* (2006.01)
(Continued)

(52) U.S. Cl.
CPC .......... *G06F 30/00* (2020.01); *A61B 17/7011* (2013.01); *A61B 34/10* (2016.02);
(Continued)

(58) Field of Classification Search
CPC ................ A61B 17/7011; A61B 34/10; A61B 2017/568; A61B 2034/105; A61B 2034/108
See application file for complete search history.

(56) References Cited

U.S. PATENT DOCUMENTS 4,382,438 A   5/1983   Jacobs
5,006,984 A   4/1991   Steele
(Continued)

FOREIGN PATENT DOCUMENTS

AU   2015258176 A1   12/2015
AU   2015202416 B2   3/2017
(Continued)

OTHER PUBLICATIONS

Aurouer, N., Obeid, I., Gille, O., Pointillart, V., & Vital, J. M. (2009). Computerized preoperative planning for correction of sagittal deformity of the spine. Surgical and radiologic anatomy, 31, 781-792. (Year: 2009).*
(Continued)

*Primary Examiner* — Bijan Mapar
(74) *Attorney, Agent, or Firm* — FOX ROTHSCHILD LLP

(57) ABSTRACT

A method and system for producing a curvature of a rod of vertebral osteosynthesis material designed to support a vertebral column of a patient is provided. A production unit receives a model defining the curvature of the rod. The curvature of the rod is based on a pre-operative X-ray of the vertical column and defined by a simulated correction to be applied to the lumbar segment to be treated, a deduced
(Continued)

curved segment representing the curvature of the rod based at least in part on one or more of a lumbar lordosis or a first curvature above a repositioned apex point and the second curvature below the repositioned apex point, and a translated curved segment representative of the deduced curve segment being translated away from a mean line of the vertebral column. The production unit uses computer aided design to produce the rod.

18 Claims, 10 Drawing Sheets

Related U.S. Application Data continuation of application No. 14/914,474, filed as application No. PCT/IB2014/064586 on Sep. 17, 2014, now Pat. No. 10,318,655.

(51) Int. Cl.
 *A61B 17/70* (2006.01)
 *A61B 34/10* (2016.01)

(52) U.S. Cl.
 CPC ... *A61B 2017/568* (2013.01); *A61B 2034/105* (2016.02); *A61B 2034/108* (2016.02)

(56) References Cited

U.S. PATENT DOCUMENTS

| | | |
|---|---|---|
| 5,011,484 A | 4/1991 | Breard |
| 5,163,440 A | 11/1992 | DeLuca et al. |
| 5,209,752 A | 5/1993 | Ashman et al. |
| 5,224,035 A | 6/1993 | Yamashita et al. |
| 5,251,127 A | 10/1993 | Raab |
| 5,291,901 A | 3/1994 | Graf |
| 5,305,203 A | 4/1994 | Raab |
| 5,312,405 A | 5/1994 | Korotko et al. |
| 5,366,455 A | 11/1994 | Dove et al. |
| 5,413,116 A | 5/1995 | Radke et al. |
| 5,514,180 A | 5/1996 | Heggeness et al. |
| 5,609,634 A | 3/1997 | Voydeville |
| 5,667,506 A | 9/1997 | Sutterlin |
| 5,748,767 A | 5/1998 | Raab |
| 5,785,663 A | 7/1998 | Sarvazyan |
| 6,015,409 A | 1/2000 | Jackson |
| 6,086,590 A | 7/2000 | Margulies et al. |
| 6,213,958 B1 | 4/2001 | Winder |
| 6,277,120 B1 | 8/2001 | Lawson |
| 6,282,437 B1 | 8/2001 | Franck et al. |
| 6,302,888 B1 | 10/2001 | Mellinger et al. |
| 6,364,849 B1 | 4/2002 | Wilcox |
| 6,385,475 B1 | 5/2002 | Cinquin et al. |
| 6,409,684 B1 | 6/2002 | Wilk |
| 6,443,953 B1 | 9/2002 | Perra et al. |
| 6,499,488 B1 | 12/2002 | Hunter et al. |
| 6,565,519 B2 | 5/2003 | Benesh |
| 6,585,666 B2 | 7/2003 | Suh et al. |
| 6,711,432 B1 | 3/2004 | Krause et al. |
| 6,716,213 B2 | 4/2004 | Shitoto |
| 6,746,449 B2 | 6/2004 | Jones et al. |
| 6,786,930 B2 | 9/2004 | Biscup |
| 7,066,938 B2 | 6/2006 | Slivka et al. |
| 7,338,526 B2 | 3/2008 | Steinberg |
| 7,509,183 B2 | 3/2009 | Lin et al. |
| 7,534,263 B2 | 5/2009 | Burdulis, Jr. et al. |
| 7,606,613 B2 | 10/2009 | Simon et al. |
| 7,611,522 B2 | 11/2009 | Gorek |
| 7,618,451 B2 | 11/2009 | Berez et al. |
| 7,634,119 B2 | 12/2009 | Tsougarakis et al. |
| 7,635,367 B2 | 12/2009 | Groiso |
| 7,639,866 B2 | 12/2009 | Pomero et al. |
| 7,660,623 B2 | 2/2010 | Hunter et al. |
| 7,674,293 B2 | 3/2010 | Kuiper et al. |
| 7,715,602 B2 | 5/2010 | Richard |
| 7,763,054 B2 | 7/2010 | Clement et al. |
| 7,824,413 B2 | 11/2010 | Varieur et al. |
| 7,835,778 B2 | 11/2010 | Foley et al. |
| 7,840,253 B2 | 11/2010 | Tremblay et al. |
| 7,862,593 B2 | 1/2011 | Clement et al. |
| 7,918,887 B2 | 4/2011 | Roche |
| 7,953,471 B2 | 5/2011 | Clayton et al. |
| 7,981,158 B2 | 7/2011 | Fitz et al. |
| 7,996,061 B2 | 8/2011 | Mollard et al. |
| 7,996,064 B2 | 8/2011 | Simon et al. |
| 8,000,926 B2 | 8/2011 | Roche et al. |
| 8,038,716 B2 | 10/2011 | Duggal et al. |
| 8,046,050 B2 | 10/2011 | Govari et al. |
| 8,066,708 B2 | 11/2011 | Lang et al. |
| 8,077,950 B2 | 12/2011 | Tsougarakis et al. |
| 8,083,778 B2 | 12/2011 | Clement et al. |
| 8,105,330 B2 | 1/2012 | Fitz et al. |
| 8,142,842 B2 | 3/2012 | Sugita et al. |
| 8,196,825 B2 | 6/2012 | Turner et al. |
| 8,211,109 B2 | 7/2012 | Groiso |
| 8,211,153 B2 | 7/2012 | Shaolian et al. |
| 8,234,097 B2 | 7/2012 | Steines et al. |
| 8,241,296 B2 | 8/2012 | Wasielewski |
| 8,246,680 B2 | 8/2012 | Betz et al. |
| 8,265,790 B2 | 9/2012 | Amiot et al. |
| 8,270,253 B1 | 9/2012 | Roche et al. |
| 8,275,594 B2 | 9/2012 | Lin et al. |
| 8,308,772 B2 | 11/2012 | Clement et al. |
| 8,308,775 B2 | 11/2012 | Clement et al. |
| 8,337,501 B2 | 12/2012 | Fitz et al. |
| 8,357,111 B2 | 1/2013 | Caillouette et al. |
| 8,357,166 B2 | 1/2013 | Aram et al. |
| 8,372,075 B2 | 2/2013 | Groiso |
| 8,377,073 B2 | 2/2013 | Wasielewski |
| 8,394,142 B2 | 3/2013 | Bertagnoli et al. |
| 8,398,681 B2 | 3/2013 | Augostino et al. |
| 8,400,312 B2 | 3/2013 | Hotokebuchi et al. |
| 8,414,592 B2 | 4/2013 | Quirno |
| 8,442,621 B2 | 5/2013 | Gorek et al. |
| 8,465,527 B2 | 6/2013 | Clement |
| 8,494,805 B2 | 7/2013 | Roche et al. |
| 8,506,632 B2 | 8/2013 | Ganem et al. |
| 8,532,806 B1 | 9/2013 | Masson |
| 8,535,337 B2 | 9/2013 | Chang et al. |
| 8,556,983 B2 | 10/2013 | Bojarski et al. |
| 8,562,653 B2 | 10/2013 | Alamin et al. |
| 8,588,892 B2 | 11/2013 | Hladio et al. |
| 8,636,776 B2 | 1/2014 | Rosenberg et al. |
| 8,672,948 B2 | 3/2014 | Lemaitre |
| 8,685,093 B2 | 4/2014 | Anderson et al. |
| 8,690,888 B2 | 4/2014 | Stein et al. |
| 8,718,820 B2 | 5/2014 | Amiot et al. |
| 8,740,941 B2 | 6/2014 | Thramann |
| 8,758,357 B2 | 6/2014 | Frey |
| 8,777,877 B2 | 7/2014 | Stein et al. |
| 8,784,339 B2 | 7/2014 | Stein et al. |
| 8,801,786 B2 | 8/2014 | Bernard et al. |
| 8,814,877 B2 | 8/2014 | Wasielewski |
| 8,814,915 B2 | 8/2014 | Hess et al. |
| 8,845,689 B2 | 9/2014 | Douget et al. |
| 8,852,237 B2 | 10/2014 | Kalfas et al. |
| 8,855,389 B1 | 10/2014 | Hoffmann et al. |
| 8,864,764 B2 | 10/2014 | Groiso |
| 8,870,889 B2 | 10/2014 | Frey |
| 8,900,316 B2 | 12/2014 | Lenz et al. |
| 8,911,448 B2 | 12/2014 | Stein |
| 8,926,673 B2 | 1/2015 | Clement et al. |
| 8,945,133 B2 | 2/2015 | Stein et al. |
| 8,956,416 B2 | 2/2015 | McCarthy |
| 8,974,467 B2 | 3/2015 | Stone |
| 8,983,813 B2 | 3/2015 | Miles et al. |
| 8,998,962 B2 | 4/2015 | Birch |
| 9,011,448 B2 | 4/2015 | Roche et al. |
| 9,034,037 B2 | 5/2015 | Fiere et al. |
| 9,039,772 B2 | 5/2015 | Park et al. |
| 9,056,017 B2 | 6/2015 | Kotlus |
| 9,066,701 B1 | 6/2015 | Finley et al. |
| 9,066,734 B2 | 6/2015 | Schoenefeld et al. |

(56) References Cited

U.S. PATENT DOCUMENTS

| | | |
|---|---|---|
| 9,078,755 B2 | 7/2015 | Mahfouz |
| 9,101,492 B2 | 8/2015 | Mangione et al. |
| 9,107,706 B2 | 8/2015 | Alamin et al. |
| 9,115,998 B2 | 8/2015 | Proulx et al. |
| 9,119,572 B2 | 9/2015 | Gorek et al. |
| 9,119,671 B2 | 9/2015 | Kast |
| 9,125,680 B2 | 9/2015 | Kostrzewski et al. |
| 9,144,470 B2 | 9/2015 | Proulx et al. |
| 9,168,153 B2 | 10/2015 | Bettenga |
| 9,173,661 B2 | 11/2015 | Metzger et al. |
| 9,180,015 B2 | 11/2015 | Fitz et al. |
| 9,192,412 B2 | 11/2015 | Meyrat et al. |
| 9,198,678 B2 | 12/2015 | Frey et al. |
| 9,232,955 B2 | 1/2016 | Bonin, Jr. et al. |
| 9,233,001 B2 | 1/2016 | Miles et al. |
| 9,237,952 B2 | 1/2016 | Kurtz |
| 9,248,023 B2 | 2/2016 | Ries et al. |
| 9,250,620 B2 | 2/2016 | Kotlus |
| 9,278,010 B2 | 3/2016 | Gibson et al. |
| 9,283,048 B2 | 3/2016 | Kostrzewski et al. |
| 9,289,221 B2 | 3/2016 | Gelaude et al. |
| 9,289,270 B2 | 3/2016 | Gielen et al. |
| 9,295,482 B2 | 3/2016 | Fitz et al. |
| 9,295,497 B2 | 3/2016 | Schoenefeld et al. |
| 9,295,561 B2 | 3/2016 | Ball et al. |
| 9,301,768 B2 | 4/2016 | Buza et al. |
| 9,308,050 B2 | 4/2016 | Kostrzewski et al. |
| 9,308,091 B2 | 4/2016 | Lang |
| 9,314,275 B2 | 4/2016 | Clement et al. |
| 9,314,343 B2 | 4/2016 | Parisi et al. |
| 9,320,547 B2 | 4/2016 | Augostino |
| 9,320,604 B2 | 4/2016 | Miles et al. |
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kuhnel |
| 9,381,085 B2 | 7/2016 | Axelson, Jr. et al. |
| 9,387,015 B2 | 7/2016 | Taylor |
| 9,392,953 B1 | 7/2016 | Gharib |
| 9,393,052 B2 | 7/2016 | Berg et al. |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,443 B2 | 9/2016 | Montello et al. |
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,032 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe, III et al. |
| 9,491,415 B2 | 11/2016 | Deitz et al. |
| 9,492,183 B2 | 11/2016 | Wilkinson et al. |
| 9,495,483 B2 | 11/2016 | Steines et al. |
| 9,495,509 B2 | 11/2016 | Amiot et al. |
| 9,498,260 B2 | 11/2016 | Funk et al. |
| 9,504,502 B2 | 11/2016 | Kuiper et al. |
| 9,510,771 B1 | 12/2016 | Finley et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,547,897 B2 | 1/2017 | Parent et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll et al. |
| 9,579,043 B2 | 2/2017 | Chien et al. |
| 9,585,597 B2 | 3/2017 | McCaulley et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agnihotri et al. |
| 9,622,712 B2 | 4/2017 | Munro et al. |
| 9,629,723 B2 | 4/2017 | Parisi et al. |
| 9,636,181 B2 | 5/2017 | Isaacs |
| 9,642,633 B2 | 5/2017 | Frey et al. |
| 9,649,170 B2 | 5/2017 | Park et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow et al. |
| 9,675,471 B2 | 6/2017 | Bojarski et al. |
| 9,693,831 B2 | 7/2017 | Mosnier et al. |
| 9,757,072 B1 | 9/2017 | Urbalejo |
| 9,782,228 B2 | 10/2017 | Mosnier et al. |
| 9,848,922 B2 | 12/2017 | Tohmeh et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,045,824 B2 | 8/2018 | Mosnier et al. |
| 10,064,656 B2 | 9/2018 | Mundis, Jr. et al. |
| 10,188,480 B2 | 1/2019 | Scholl et al. |
| 10,201,320 B2 | 2/2019 | Saget et al. |
| 10,219,865 B2 | 3/2019 | Jansen et al. |
| 10,314,657 B2 | 6/2019 | Mosnier et al. |
| 10,318,655 B2 | 6/2019 | Mosnier et al. |
| 10,413,365 B1 | 9/2019 | Mosnier et al. |
| 10,420,615 B1 | 9/2019 | Mosnier et al. |
| 10,433,912 B1 | 10/2019 | Mosnier et al. |
| 10,433,913 B2 | 10/2019 | Mosnier et al. |
| 10,441,363 B1 | 10/2019 | Mosnier et al. |
| 10,456,174 B2 | 10/2019 | Mickiewicz et al. |
| 10,456,211 B2 | 10/2019 | McAfee |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0068936 A1 | 6/2002 | Burkus et al. |
| 2002/0103432 A1 | 8/2002 | Kawchuk |
| 2003/0191383 A1 | 10/2003 | Ben-Haim et al. |
| 2003/0204189 A1 | 10/2003 | Cragg |
| 2004/0120781 A1 | 6/2004 | Luca et al. |
| 2004/0143243 A1 | 7/2004 | Wahrburg |
| 2004/0152972 A1 | 8/2004 | Hunter |
| 2004/0167637 A1 | 8/2004 | Biscup |
| 2004/0171924 A1 | 9/2004 | Mire et al. |
| 2004/0172020 A1 | 9/2004 | Beaurain et al. |
| 2004/0215190 A1 | 10/2004 | Nguyen et al. |
| 2004/0243148 A1 | 12/2004 | Wasielewski |
| 2004/0267279 A1 | 12/2004 | Casutt et al. |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Gharib et al. |
| 2005/0203531 A1 | 9/2005 | Lakin et al. |
| 2005/0203532 A1 | 9/2005 | Ferguson |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0036259 A1 | 2/2006 | Carl et al. |
| 2006/0069324 A1 | 3/2006 | Block et al. |
| 2006/0074431 A1* | 4/2006 | Sutton .............. A61B 17/025 606/90 |
| 2006/0136058 A1 | 6/2006 | Pietrzak |
| 2006/0142657 A1 | 6/2006 | Quaid et al. |
| 2006/0285991 A1 | 12/2006 | McKinley |
| 2006/0287627 A1 | 12/2006 | Johnson |
| 2007/0021682 A1 | 1/2007 | Gharib et al. |

(56) References Cited

U.S. PATENT DOCUMENTS

| | | |
|---|---|---|
| 2007/0118243 A1 | 5/2007 | Schroeder et al. |
| 2007/0173818 A1 | 7/2007 | Hestad et al. |
| 2007/0225731 A1 | 9/2007 | Couture et al. |
| 2008/0009866 A1 | 1/2008 | Alamin et al. |
| 2008/0058945 A1 | 3/2008 | Hajaj et al. |
| 2008/0108991 A1 | 5/2008 | von Jako |
| 2008/0177203 A1 | 7/2008 | von Jako |
| 2008/0245972 A1 | 10/2008 | Drapeau |
| 2008/0255575 A1 | 10/2008 | Justis et al. |
| 2008/0262549 A1 | 10/2008 | Bennett et al. |
| 2008/0281332 A1 | 11/2008 | Taylor |
| 2009/0024164 A1 | 1/2009 | Neubardt |
| 2009/0076615 A1 | 3/2009 | Duggal et al. |
| 2009/0194206 A1 | 8/2009 | Jeon et al. |
| 2009/0204159 A1 | 8/2009 | Justis et al. |
| 2009/0248080 A1 | 10/2009 | Wilcox et al. |
| 2009/0249851 A1 | 10/2009 | Isaacs |
| 2009/0254326 A1 | 10/2009 | Isaacs |
| 2009/0264932 A1 | 10/2009 | Alamin et al. |
| 2010/0042157 A1 | 2/2010 | Trieu |
| 2010/0100011 A1 | 4/2010 | Roche |
| 2010/0191071 A1 | 7/2010 | Anderson et al. |
| 2010/0191088 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 1/2011 | Holm |
| 2011/0071802 A1 | 3/2011 | Bojarski et al. |
| 2011/0106163 A1 | 5/2011 | Hochschuler et al. |
| 2011/0118740 A1 | 5/2011 | Rabiner et al. |
| 2011/0137345 A1 | 6/2011 | Stoll et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0295378 A1 | 12/2011 | Bojarski et al. |
| 2011/0306873 A1 | 12/2011 | Shenai et al. |
| 2012/0022357 A1 | 1/2012 | Chang et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0150243 A9 | 6/2012 | Crawford et al. |
| 2012/0165872 A1 | 6/2012 | Alamin et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0268007 A1 | 10/2013 | Rezach et al. |
| 2013/0303883 A1 | 11/2013 | Zehavi et al. |
| 2013/0345718 A1 | 12/2013 | Crawford et al. |
| 2014/0058407 A1 | 2/2014 | Tsekos et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0277149 A1 | 9/2014 | Rooney et al. |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Taylor |
| 2015/0100066 A1 | 4/2015 | Kostrzewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe, III et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mafhouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin et al. |
| 2016/0038307 A1 | 2/2016 | Bettenga |
| 2016/0045230 A1 | 2/2016 | Lowery et al. |
| 2016/0045317 A1 | 2/2016 | Lang et al. |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0228192 A1 | 8/2016 | Jansen et al. |
| 2016/0235447 A1 | 8/2016 | Mundis, Jr. et al. |
| 2016/0235480 A1 | 8/2016 | Scholl et al. |
| 2016/0235493 A1 | 8/2016 | LeBoeuf, II et al. |
| 2016/0242819 A1 | 8/2016 | Simpson et al. |
| 2016/0242857 A1 | 8/2016 | Scholl |
| 2016/0242934 A1 | 8/2016 | van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | Lavallee et al. |
| 2016/0283676 A1 | 9/2016 | Lyon et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasielewski |
| 2017/0119472 A1 | 5/2017 | Herrmann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0135770 A1 | 5/2017 | Scholl et al. |
| 2017/0143426 A1 | 5/2017 | Isaacs et al. |

(56) References Cited

U.S. PATENT DOCUMENTS

| | | |
|---|---|---|
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0231661 A1 | 8/2017 | Bannigan et al. |
| 2017/0231709 A1 | 8/2017 | Gupta et al. |
| 2017/0252107 A1 | 9/2017 | Turner et al. |
| 2017/0273718 A1 | 9/2017 | Metzger et al. |
| 2017/0360493 A1 | 12/2017 | Zucker et al. |
| 2018/0078286 A1 | 3/2018 | Le Couedic et al. |
| 2018/0178148 A1 | 6/2018 | Mazor et al. |
| 2018/0256067 A1 | 9/2018 | Chien et al. |
| 2018/0289396 A1 | 10/2018 | McGahan et al. |
| 2018/0295584 A1 | 10/2018 | Gliner et al. |
| 2018/0301213 A1 | 10/2018 | Zehavi et al. |
| 2018/0303552 A1 | 10/2018 | Ryan et al. |
| 2018/0310993 A1 | 11/2018 | Hobeika et al. |
| 2019/0015136 A1 | 1/2019 | Kraemer |
| 2019/0029733 A1 | 1/2019 | Mickiewicz et al. |
| 2019/0046269 A1 | 2/2019 | Hedblom et al. |
| 2019/0046287 A1 | 2/2019 | Fallin et al. |
| 2019/0059951 A1 | 2/2019 | Barrus |
| 2019/0060086 A1 | 2/2019 | Krause et al. |
| 2019/0069956 A1 | 3/2019 | Ryan et al. |
| 2019/0083144 A1 | 3/2019 | Sharifi-Mehr et al. |
| 2019/0099221 A1 | 4/2019 | Schmidt et al. |
| 2019/0103190 A1 | 4/2019 | Schmidt et al. |
| 2019/0110819 A1 | 4/2019 | Triplett et al. |
| 2019/0117278 A1 | 4/2019 | Chin |
| 2019/0122364 A1 | 4/2019 | Zhang et al. |
| 2019/0142599 A1 | 5/2019 | Thibodeau |
| 2019/0167314 A1 | 6/2019 | Mosnier et al. |
| 2019/0201013 A1 | 7/2019 | Siccardi et al. |
| 2019/0201155 A1 | 7/2019 | Gupta et al. |
| 2019/0216507 A1 | 7/2019 | Bannigan et al. |
| 2019/0223916 A1 | 7/2019 | Barrus et al. |
| 2019/0231435 A1 | 8/2019 | Zucker et al. |
| 2019/0231443 A1 | 8/2019 | McGinley et al. |
| 2019/0231557 A1 | 8/2019 | Sutterlin, III et al. |
| 2019/0239935 A1 | 8/2019 | Willis et al. |
| 2019/0247100 A1 | 8/2019 | Mundis, Jr. et al. |
| 2019/0254719 A1 | 8/2019 | Gandhi et al. |
| 2019/0262015 A1 | 8/2019 | Siccardi et al. |
| 2019/0269463 A1 | 9/2019 | Mosnier et al. |
| 2019/0380782 A1 | 12/2019 | McAfee et al. |
| 2020/0060768 A1 | 2/2020 | Mosnier et al. |
| 2020/0121394 A1 | 4/2020 | Mosnier et al. |
| 2020/0170676 A1 | 6/2020 | Grob |
| 2020/0315708 A1 | 10/2020 | Mosnier et al. |

FOREIGN PATENT DOCUMENTS

| | | |
|---|---|---|
| AU | 2019200740 A1 | 2/2019 |
| AU | 2019200888 A1 | 2/2019 |
| AU | 2014363945 B2 | 4/2019 |
| AU | 2019203557 A1 | 6/2019 |
| CA | 2872845 A1 | 11/2013 |
| CA | 2927955 A1 | 4/2014 |
| CN | 1816134 A | 8/2006 |
| CN | 102805677 A | 12/2012 |
| CN | 104127229 A | 11/2014 |
| CN | 205073000 U | 3/2016 |
| CN | 103892953 B | 5/2016 |
| CN | 104323843 B | 1/2017 |
| CN | 104434287 B | 1/2017 |
| CN | 105078555 B | 9/2018 |
| EP | 1 570 781 A1 | 9/2005 |
| EP | 2 053 580 A1 | 4/2009 |
| EP | 2 749 235 A1 | 7/2014 |
| EP | 2 754 419 A2 | 7/2014 |
| EP | 2 496 183 B1 | 9/2015 |
| EP | 3 000 443 A2 | 3/2016 |
| EP | 2 608 749 B1 | 8/2016 |
| EP | 2 403 434 B1 | 4/2017 |
| EP | 3 395 281 A1 | 10/2018 |
| EP | 3 431 032 A1 | 1/2019 |
| FR | 1358988 A | 4/1964 |
| FR | 1360208 A | 5/1964 |
| JP | 2016-537036 A | 12/2016 |
| JP | 2016-540610 A | 12/2016 |
| SU | 1497721 A1 | 7/1989 |
| SU | 1704102 A1 | 1/1992 |
| WO | 9855038 A1 | 12/1998 |
| WO | 00/53077 A2 | 9/2000 |
| WO | 04/017836 A2 | 3/2004 |
| WO | 04/030559 A1 | 4/2004 |
| WO | 04/089224 A2 | 10/2004 |
| WO | 04/111948 A2 | 12/2004 |
| WO | 05/074368 A2 | 8/2005 |
| WO | 06/075331 A2 | 7/2006 |
| WO | 06/084193 A2 | 8/2006 |
| WO | 07/035925 A2 | 3/2007 |
| WO | 07/038290 A2 | 4/2007 |
| WO | 08/002588 A2 | 1/2008 |
| WO | 08/079546 A2 | 7/2008 |
| WO | 08/124079 A1 | 10/2008 |
| WO | 09/119181 A1 | 10/2009 |
| WO | 09/124245 A1 | 10/2009 |
| WO | 10/044880 A1 | 4/2010 |
| WO | 10/064234 A2 | 6/2010 |
| WO | 10/121147 A1 | 10/2010 |
| WO | 10/147972 A1 | 12/2010 |
| WO | 11/021192 A1 | 2/2011 |
| WO | 12/012863 A1 | 2/2012 |
| WO | 12/113030 A1 | 8/2012 |
| WO | 12/131660 A1 | 10/2012 |
| WO | 13/003435 A1 | 1/2013 |
| WO | 14/191790 A1 | 12/2014 |
| WO | 15/040552 A1 | 3/2015 |
| WO | 15/054543 A1 | 4/2015 |
| WO | 15/056131 A1 | 4/2015 |
| WO | 15/079011 A1 | 6/2015 |
| WO | 15/089118 A1 | 6/2015 |
| WO | 15/185219 A1 | 12/2015 |
| WO | 15/195843 A2 | 12/2015 |
| WO | 15/200720 A2 | 12/2015 |
| WO | 16/012726 A1 | 1/2016 |
| WO | 16/019424 A1 | 2/2016 |
| WO | 16/019425 A1 | 2/2016 |
| WO | 16/019426 A1 | 2/2016 |
| WO | 16/26053 A1 | 2/2016 |
| WO | 16/032875 A1 | 3/2016 |
| WO | 16/044352 A1 | 3/2016 |
| WO | 16/048800 A1 | 3/2016 |
| WO | 16/088130 A1 | 6/2016 |
| WO | 16/094826 A1 | 6/2016 |
| WO | 16/102026 A1 | 6/2016 |
| WO | 16/137347 A1 | 9/2016 |
| WO | 16/148675 A1 | 9/2016 |
| WO | 16/165030 A1 | 10/2016 |
| WO | 17/001851 A1 | 1/2017 |
| WO | 17/039596 A1 | 3/2017 |
| WO | 17/064719 A1 | 4/2017 |
| WO | 17/066518 A1 | 4/2017 |
| WO | 17/077356 A1 | 5/2017 |
| WO | 17/079655 A2 | 5/2017 |
| WO | 17/127838 A1 | 7/2017 |
| WO | 17/151949 A1 | 9/2017 |
| WO | 17/221257 A1 | 12/2017 |
| WO | 18/045086 A1 | 3/2018 |
| WO | 18/055494 A1 | 3/2018 |
| WO | 18/055518 A1 | 3/2018 |
| WO | 18/078636 A1 | 5/2018 |
| WO | 18/087758 A1 | 5/2018 |
| WO | 18/131044 A1 | 7/2018 |
| WO | 18/131045 A1 | 7/2018 |
| WO | 18/183314 A1 | 10/2018 |
| WO | 18/185755 A1 | 10/2018 |
| WO | 18/193316 A2 | 10/2018 |
| WO | 18/193317 A1 | 10/2018 |
| WO | 18/203101 A1 | 11/2018 |
| WO | 2019014452 A1 | 1/2019 |
| WO | 2019036039 A2 | 2/2019 |
| WO | 2019043426 A1 | 3/2019 |

(56) References Cited

FOREIGN PATENT DOCUMENTS

| WO | 2019068085 A1 | 4/2019 |
|---|---|---|
| WO | 2019070729 A1 | 4/2019 |
| WO | 2019118844 A1 | 6/2019 |
| WO | 2019140240 A1 | 7/2019 |

OTHER PUBLICATIONS

Aurouer et al. "Computerized preoperative planning for correction of sagittal deformity of the spine", Surg Radiol Anat 31, 2009, pp. 781-792. (Year: 2009).
Abe et al. "Scoliosis corrective force estimation from the implanted rod deformation using 3 D FEM analysis", 2015, Scoliosis 10(Suppl 2):52, 6 pages.
Aubin et al. "Preoperative Planning Simulator for Spinal Deformity Surgeries", Spine 2008, 33(20):2143-2152.
Reinshagen et al. "A novel minimally invasive technique for lumbar decompression, realignment, and navigated interbody fusion", J Clin Neurosci. 2015, 22(9):1484-1490: XP055503028.
Rickert et Al., "Posterior lumbar interbody fusion implants", Orthopaede. Springer Verlag, Berlin, DE vol. 44, No. 2 dated Jan. 28, 2015 pp. 162-169.
Spontech Medical AG Vertaplan—die Software fiir Wirbelsaulenchirurgen, Aug. 29, 2013 Retrieved from the Internet: URL: <https://www.youtube.com/watch?v=q0qhW1T1cp8> in 1 page.
Barton et al., Mar./Apr. 2016, Early experience and initial outcomes with patient-specific spine rods for adult spinal deformity, Trending in Orthopedics, 39(2):79-86.
Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer International Publishing, Switzerland, pp. 645-662.
Foroozandeh et al., Summer 2012, 3D reconstruction using cubic Bezier spline curves and active contours (case study), Iranian Journal of Medical Physics, 9(3):169-176.
Galbusera et al., Feb. 2019, Artificial intelligence and machine learning in spine research, JOR Spine, 2:E1044, 20 pp.
Grove, 2011, Heterogeneous modeling of medical image data using B-spline functions, doctoral dissertation, Department of Computer Science and Engineering, University of South Florida, 212 pp.
Lazarus, Jun. 21, 2013, An introduction to splines, 29 pp.
Li et al., 2009, Modeling and measurement of 3D deformation of scoliotic spine using 2D x-ray images, Lecture Notes in Computer Science, 8 pp.
Lin, Sep. 17-21, 2003, The simplified spine modeling by 3-D Bezier curve based on the orthogonal spinal radiographic images, Proceedings of the 25th Annual International Conference of the IEEE EMBS, Cancun, Mexico, pp. 944-946.
Pasha et al., 2018, Data-driven classification of the 3D spinal curve in adolescent idiopathic scoliosis with an applications in surgical outcome prediction, Scientific Reports, 8:16296, 10 pp.
Poredos et al., 2015, Determination of the human spine curve based on laser triangulation, BMC Medical Imaging 15(2):1-11.
Prautzsch et al., Mar. 26, 2001, Bezier-and B-spline techniques, 58 pp.
Ratnakar et al. 2011, Predicting thoracic spinal postures in finite element model with Bezier technique, Ircobe Conference 2011, IRC-11-57, 4 pp.
Solla et al., Mar. 2019, Patient-specific rods for surgical correction of sagittal imbalance in adults: Technical aspects and preliminary results: Clin Spine Surg, 32(2): 7 pp.
International Search Report in PCT Application PCT/IB2014/064586, dated Dec. 23, 2014, in 2 pages.
International Search Report in POT Application PCT/US2016/060676, dated Nov. 5, 2017 in 7 pages.
International Search Report and Written Opinion in PCT Application PCT/IB2018/000551, dated Dec. 12, 2018 in 9 pages.

* cited by examiner

METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT'S VERTEBRAL COLUMN

CROSS-REFERENCE TO RELATED APPLICATION

This application is continuation U.S. serial application Ser. No. 16/389,348, filed Apr. 19, 2019, which is a continuation of U.S. Serial application Ser. No. 14/914,474, filed Feb. 25, 2016, now U.S. Pat. No. 10,318,655, which is a national stage entry of PCT/IB2014/064586 filed Sep. 17, 2014, under the International Convention claiming priority over French Patent Application No. 1358988 filed Sep. 18, 2013, all of which are incorporated herein by reference in their entirely.

FIELD OF THE INVENTION

The present invention relates to a method making it possible to produce the ideal curvature of a rod of vertebral osteosynthesis material designed to support a patient's vertebral column.

BACKGROUND OF THE INVENTION

It is known to analyze a patient's vertebral column in reference to so-called "pelvic" parameters and different morphotypes of a vertebral column, documented in the scientific literature. The appended FIG. 1 very diagrammatically shows the base of the vertebral column, i.e., part of the lumbar vertebrae L and the sacrum S, as well as the femoral heads TF; the aforementioned pelvic criteria are:
- the SS (sacral slope) criterion, which is the incline angle of the plate of S1 (first vertebra of the sacrum), relative to the horizontal;
- the PV (pelvic version) criterion, which is the angle formed by the straight segment connecting the center of the femoral heads TF and the center of the plate of S1 with the vertical;
- the PI (pelvic incidence) criterion, which is the angle formed by the straight segment connecting the center of the femoral heads TF and the center of the plate of S1 with the perpendicular to the plate of S1.

FIGS. 2A to 2D respectively show:
- a so-called "type 1" morphotype, in which the apex (i.e., the forwardmost point of the vertebral column) is situated at the median plane of L5 (fifth lumbar vertebra), and the SS criterion corresponds to an angle smaller than 35°;
- a so-called "type 2" morphotype, in which the apex is situated at the base of L4 (fourth lumbar vertebra), and the SS criterion corresponds to an angle smaller than 35°;
- a so-called "type 3" morphotype, in which the apex is situated at the median plane of L4, and the SS criterion corresponds to an angle comprised between 35° and 45°;
- a so-called "type 4" morphotype, in which the apex is situated at the base of L3 (third lumbar vertebra), and the SS criterion corresponds to an angle larger than 45°.

It is accepted that an individual will adopt a natural vertebral column posture, called "economic", avoiding pain and other pathologies, if his pelvic parameters in particular are in agreement with his back morphotype. If this is not the case, surgical treatment may be considered in order to reestablish proper posture of the vertebral column, in which that agreement exists.

It is well known to perform this type of recovery using rigid vertebral rods, in particular made of metal, fastened to the vertebrae using anchor members such as pedicle screws or laminar hooks, which rods must be curved suitably based on the correction to be done. The publication of patent application No. WO 98/55038 illustrates material of this type.

It has been shown that imparting the appropriate curvature to a straight rod may be very difficult for a surgeon, the curvature being more or less pronounced in any given location of the rod. Currently, such a curvature is done at the surgeon's discretion and calls greatly on the latter's experience and dexterity. The trial and error necessary to obtain an appropriate curvature have the significant drawback of extending the operation time, which is not desirable for the patient, and the risk of implanting a rod with a non-ideal curvature cannot be ruled out.

OBJECTS OF THE INVENTION

The present invention aims to resolve this essential drawback.

The patent application publications No. WO 2004/017836 A2, WO 2009/254326 A1 and US 2008/079546 A2 describe methods that do not achieve this goal satisfactorily.

SUMMARY OF THE INVENTION

To that end, the method according to the invention comprises the following steps:
a) taking a sagittal preoperative x-ray of the vertebral column of the patient to be treated, extending from the cervical vertebrae to the femoral heads;
b) on that x-ray, identifying: the so-called "pelvic" parameters, i.e., the sacral slope, the pelvic version and the pelvic incidence,
   the lumbar lordosis,
   the position of the apical lumbar vertebra, i.e., that situated furthest forward on the x-ray,
   at least one of the following measurements:
   - the distance, called SVA, from the vertical of the posterior upper point of the plate of the first vertebra of the sacrum, called S1, to the vertical passing through the center of the 7th cervical vertebra;
   - the distance, called SFD, from the vertical of the posterior upper point of the plate of S1 to the vertical passing through the center of the femoral heads;
   - the angle, called T1/SPI, formed between the segment going from the center of the first dorsal vertebra, called T1, to the center of the femoral heads and the vertical to the center of T1, a cloud of points defining the curvature of the patient's vertebral column, including one point per vertebral level, positioned at the center of the upper plate of an affected vertebra, and a point defining the noted preoperative apex;
c) deducing, among predetermined vertebral column morphotypes and from the noted value of the sacral slope, the morphotype to which the treated vertebral column corresponds and deducing the desired postoperative apex point after performing the correction therefrom, and defining the vertebrae in which the anchor members for the vertebral rod to be anchored to the vertebrae will be implanted;

d) performing a wire modeling of the patient's vertebral column, for example using CAD software;

e) defining, from said pelvic parameters, a reference centered at the plate of S1, the origin point of which is the central point of that plate;

f) positioning the different points of said cloud of points, attached to each vertebra, in that reference, and drawing arcs step by step between the identified points, all of the arcs being tangent to each other and the arc extending from S1 being tangent to the straight line perpendicular to the plate of S1;

g) reading the values of the arc lengths;

h) simulating the correction to be applied to the lumbar segment to be treated as follows:

h1) drawing a straight line tangent to the desired postoperative apex point, moving that straight line to a vertical position such that the arc attached to that straight line is tangent to the desired postoperative apex point, the latter thus being repositioned so as to become the apex point of the modeled vertebral column segment, h2) defining, as co-radial to each other, the arcs situated below that apex point and defining as co-radial to each other the arcs situated above that same apex point, so as to obtain two different curvatures, one above that apex point and the other below the apex point, h3) defining the lumbar lordosis as being equal to plus or minus ten degrees of the pelvic incidence, and defining one of the following three values as desired:
SVA distance smaller than 5 cm;
SVA/SFD ratio comprised between −1.9 and +0.1; the value of this ratio is positive on the side of the vertical of the posterior upper point of the plate of S1 situated toward the femoral heads and is negative on the side of the vertical situated opposite the femoral heads;
T1/SPI angle comprised between −9° and 0°, that angle being negative on the side of the vertical at the center of T1 located toward the femoral heads;

h4) defining two arcs concentric to the two curvatures obtained during step h2 above, which are tangent to each other at the apex point, those arcs forming a curved segment representing the ideal curvature of the rod to be implanted in order to obtain the correction of the vertebral segment to be treated, h5) translating that curved segment away from the mean line of the vertebral column, over an evaluated mean distance going from the center of the vertebrae to the anchor points of the anchor members for anchoring the rod to the vertebrae of said vertebral segment to be treated, such that the position of said curve segment corresponds to the position the rod will assume once implanted;

i) defining the diameter of the rod to be implanted;

j) defining a two- or three-dimensional model of the rod, curved along said curve segment, and k) from a straight rod, producing the curvature of that rod according to said model.

Preferably, said predetermined vertebral column morphotypes comprise:

a so-called "type 1" morphotype, in which the apex (i.e., the forwardmost point of the vertebral column) is situated at the median plane of L5 (fifth lumbar vertebra), and the SS criterion corresponds to an angle smaller than 35°;

a so-called "type 2" morphotype, in which the apex is situated at the base of L4 (fourth lumbar vertebra), and the SS criterion corresponds to an angle smaller than 35°;

a so-called "type 3" morphotype, in which the apex is situated at the median plane of L4, and the SS criterion corresponds to an angle comprised between 35° and 45°;

a so-called "type 4" morphotype, in which the apex is situated at the base of L3 (third lumbar vertebra), and the SS criterion corresponds to an angle larger than 45°.

Preferably, the two- or three-dimensional modeling done in step j) consists of establishing a drawing or a plan of the rod to be produced.

Preferably, the curvature produced in step k) is done by cold bending.

Preferably, the method comprises, after step h5) or step i) or step j), the transfer of data relative to the rod to be produced to a service provider responsible for producing the curvature of the rod.

Thus, a practitioner, having determined the shape of the rod to be implanted using the method according to the invention, transfers the data relative to the rod to be produced to a service provider responsible for producing the curvature of the rod. Once that curvature is produced, the service provider will deliver the curved rod to the practitioner, who will be able to operate on the patient with his vertebral rod that is ready to be implanted.

The invention will be well understood, and other features and advantages thereof will appear, in reference to the appended diagrammatic drawing, showing, as a non-limiting example, different values used to carry out the method in question and different operations performed in the context of that implementation.

DETAILED DESCRIPTION OF THE PREFERRED EMBODIMENT

Figure 1:
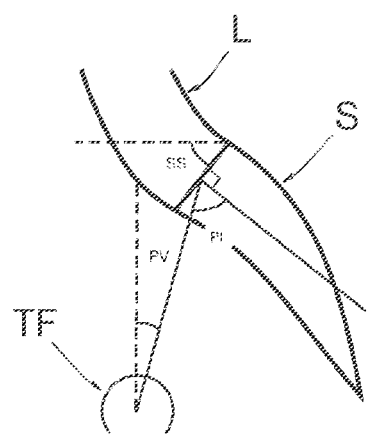
FIG. 1 very diagrammatically shows the base of the vertebral column.
Figure 2A:
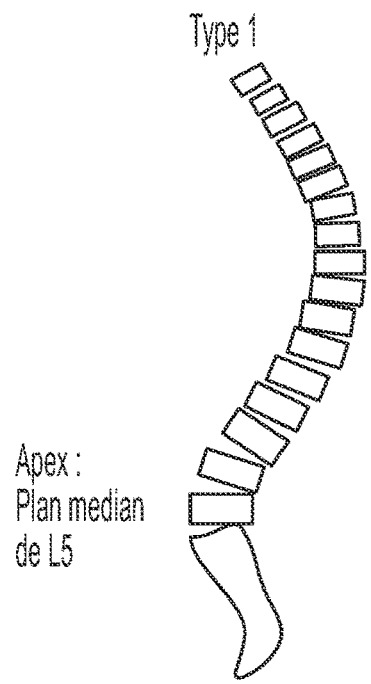
FIG. 2A shows a so-called "type 1" morphotype, in which the apex is situated at the median plane of L5 and the SS criterion corresponds to an angle smaller than 35°.
Figure 2B:
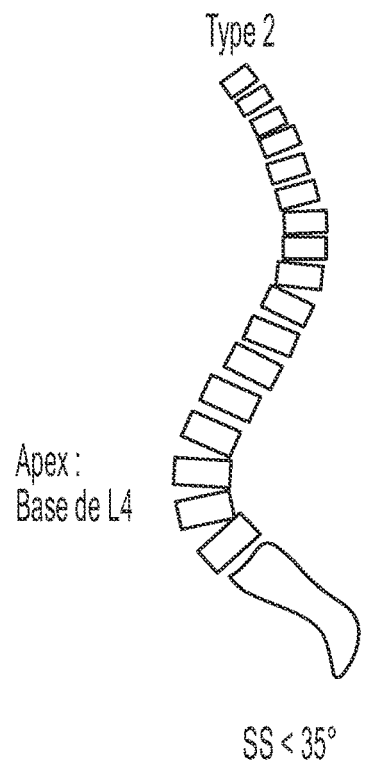
FIG. 2B shows a so-called "type 2" morphotype, in which the apex is situated at the base of L4 and the SS criterion corresponds to angle smaller than 35°.
Figure 2C:
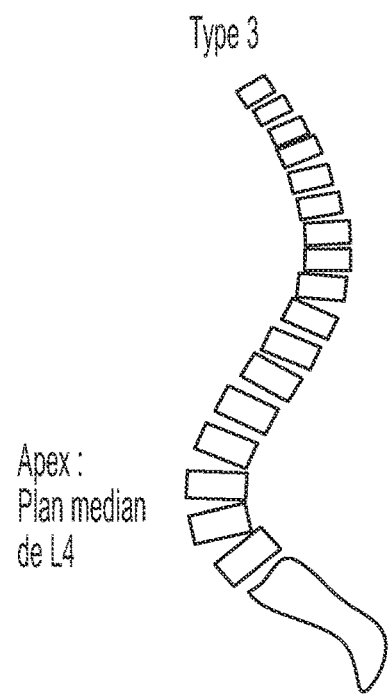
FIG. 2C shows a so-called "type 3" morphotype, in which the apex is situated at the median plane of L4 and the SS criterion corresponds to angle comprised between 35° and 45°.
Figure 2D:
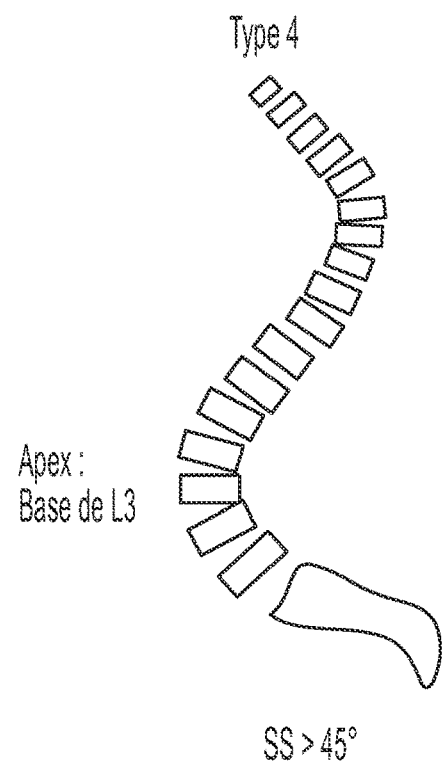
FIG. 2D shows a so-called "type 4" morphotype, in which the apex is situated at the base of L3 and the SS criterion corresponds to angle larger than 45°.
Figure 3:
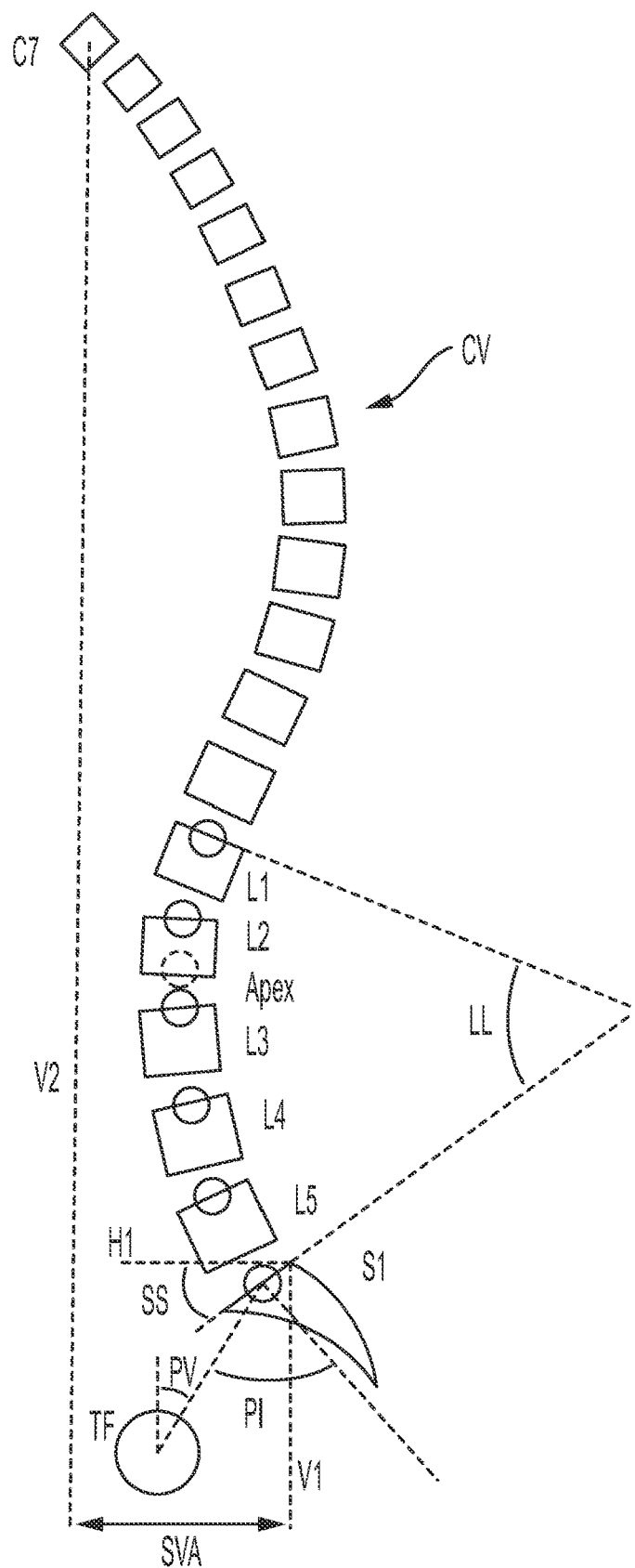
FIG. 3 is a very diagrammatic view of a vertebral column, on which the definition points of an SVA value used to implement the method according to the invention are shown.

FIG. 3 very diagrammatically shows a vertebral column CV, and includes the following information:
LL: vertebral segment to be treated;
L1, L2, L3, L4, L5, S1, C7: the first, second, third, fourth and fifth lumbar vertebrae, the first vertebra of the sacrum and the seventh cervical vertebra, respectively;
Apex: the forward most point of the vertebral column; SS, PV, Pl: the aforementioned pelvic criteria;
TF: the femoral heads, shown by a circle;
H1 and V1: the horizontal and vertical, respectively, at the posterior upper point of the plate of S1;
V2: the vertical passing through the center of the 7th cervical vertebra (C7).

Figure 4:
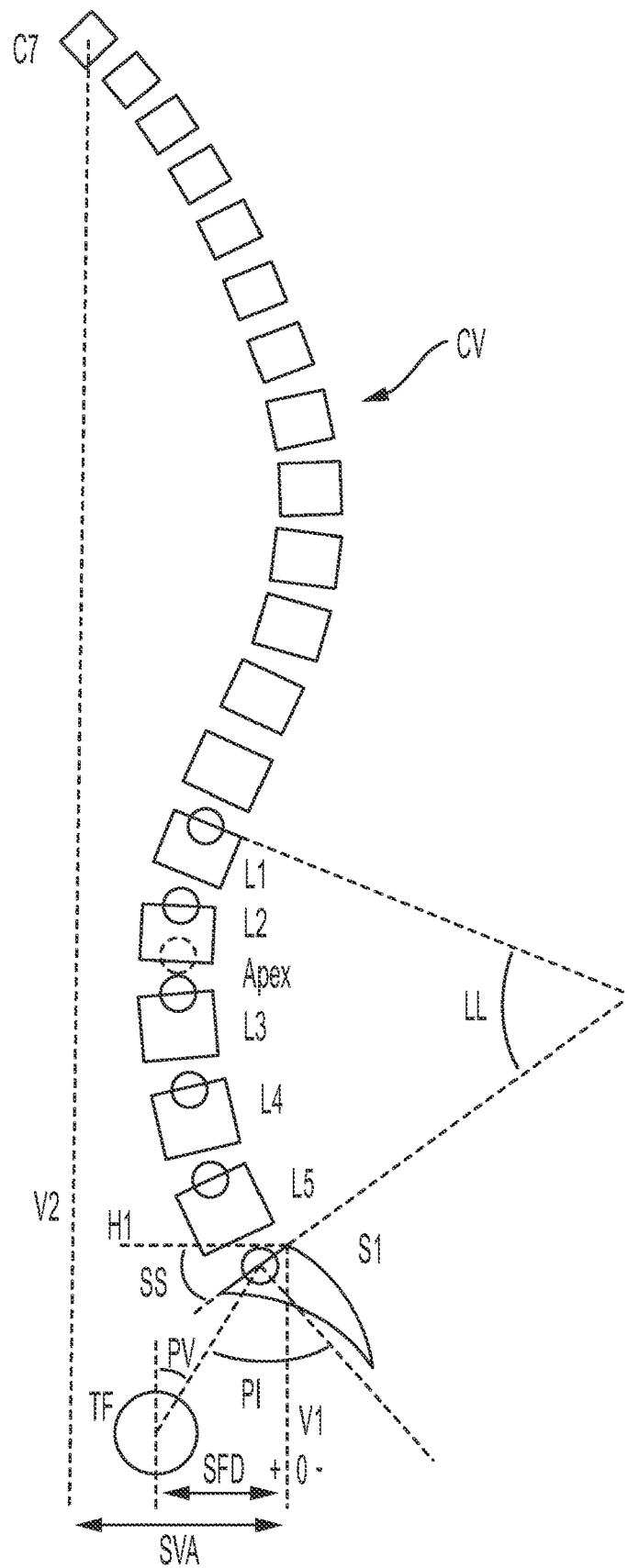
FIG. 4 is a view similar to FIG. 3, which shows the definition points of the SVA value and an SFD value, those two values being used to define a ratio employed to carry out the method according to the invention.

FIG. 4 also mentions a so-called "SFD" value, going from the vertical V1 to the vertical passing through the center of the femoral heads TF.

Figure 5:
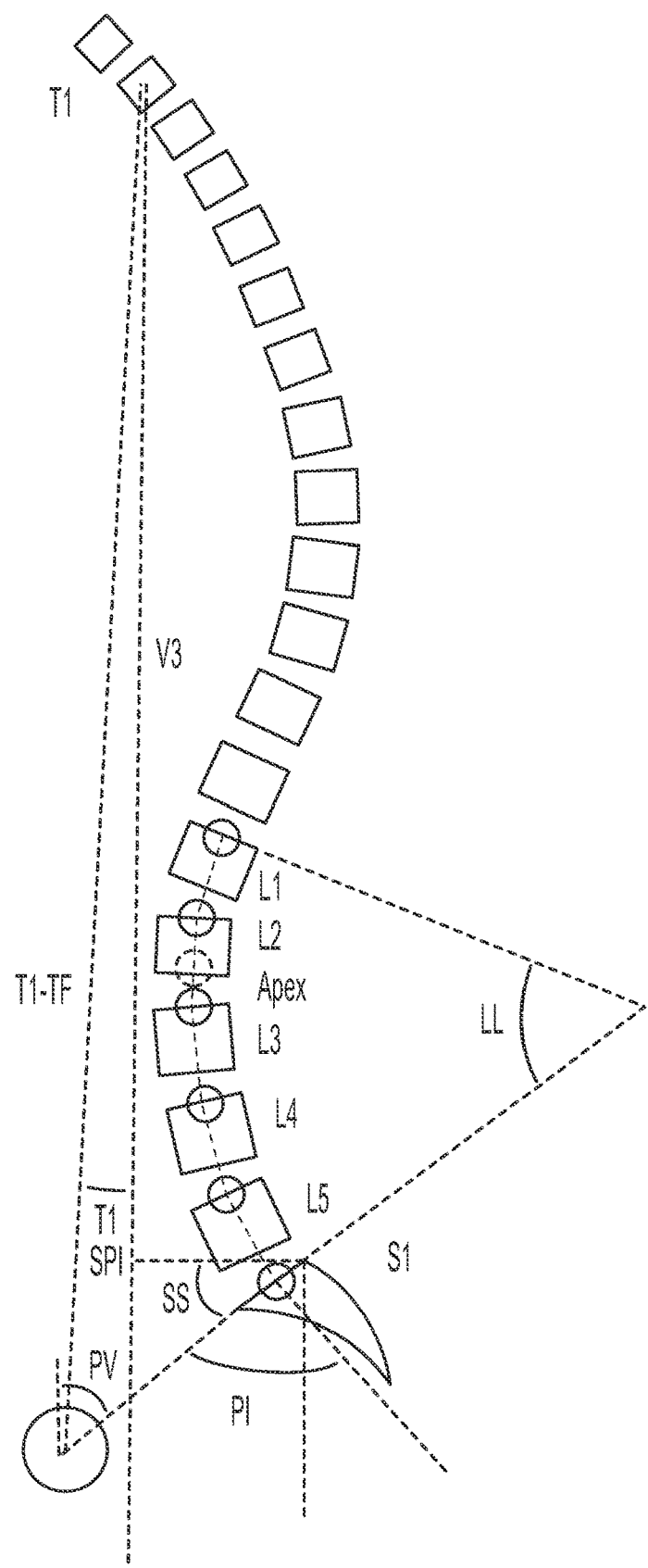
FIG. 5 is a view similar to FIG. 3, showing the definition points of a so-called T1/SPI value used to carry out the method according to the invention.

FIG. 5 also mentions a so-called "T1/SPI" value, which is the angle formed between the T1-TF segment going from the center of the first dorsal vertebra, called T1, to the center of the femoral heads TF and the vertical V3 to the center of T1.

The various steps of the method are illustrated in FIGS. 6 to 11 as follows.

Figure 6:
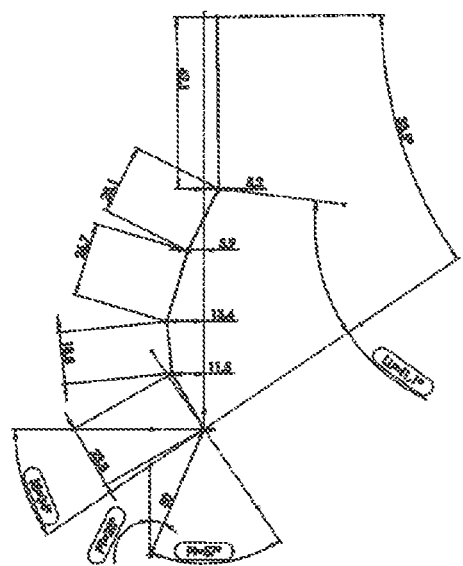
FIGS. 6 to 11 are very diagrammatic views of reference points, segments, arcs of circle and curves used during the different successive steps of this method.

FIG. 6: on a sagittal preoperative x-ray of the vertebral column of the patient to be treated, extending from the cervical vertebrae to the femoral heads, the following are identified:
the pelvic parameters,
the lumbar lordosis, the position of the apical lumbar vertebra, i.e., that situated furthest forward on the x-ray,
as desired, the SVA distance only, or the SVA distance and the SFD distance,
a cloud of points defining the curvature of the patient's vertebral column, including one point per vertebral level, positioned at the center of the upper plate of an affected vertebra, and a point defining the noted preoperative apex.

The morphotype to which the treated vertebral column corresponds is deduced on the noted points, among the vertebral column morphotypes shown in FIGS. 2A to 2D, from the value of the noted sacral slope; the desired postoperative apex point after performing the correction is deduced therefrom; the vertebrae in which the anchoring members for the vertebral rod to be anchored to the vertebrae will be implanted are also defined in this step.

Figure 7:
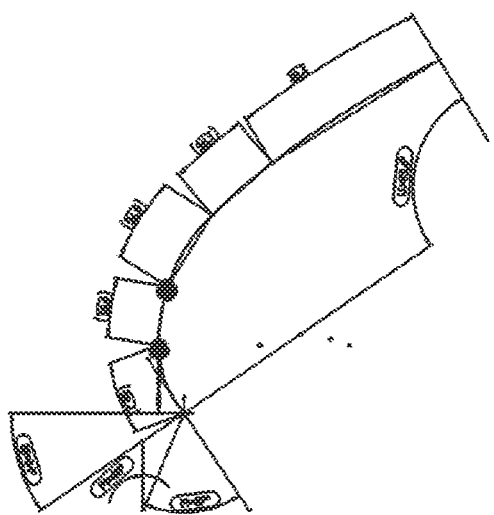
Figure 8:
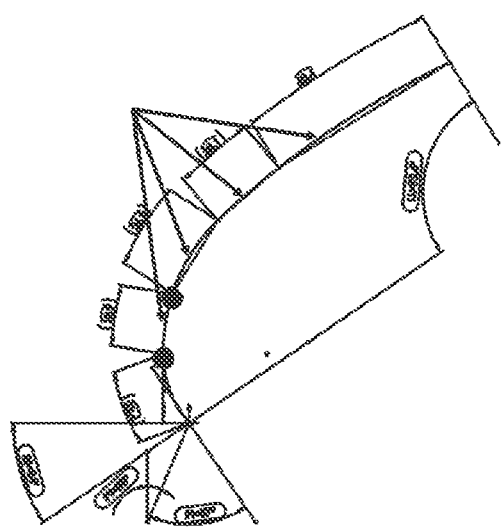
Figure 9:
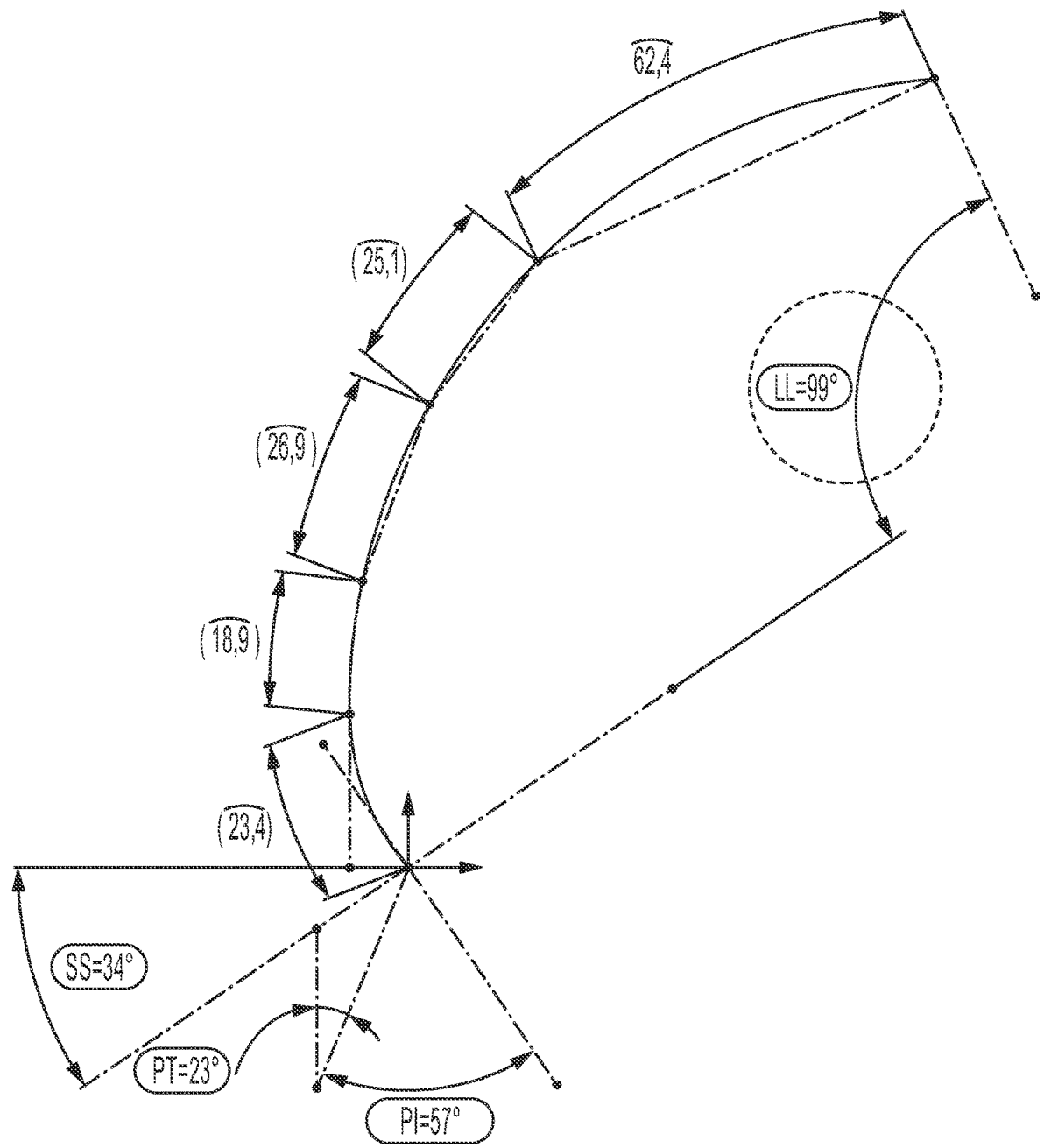
Figure 10:
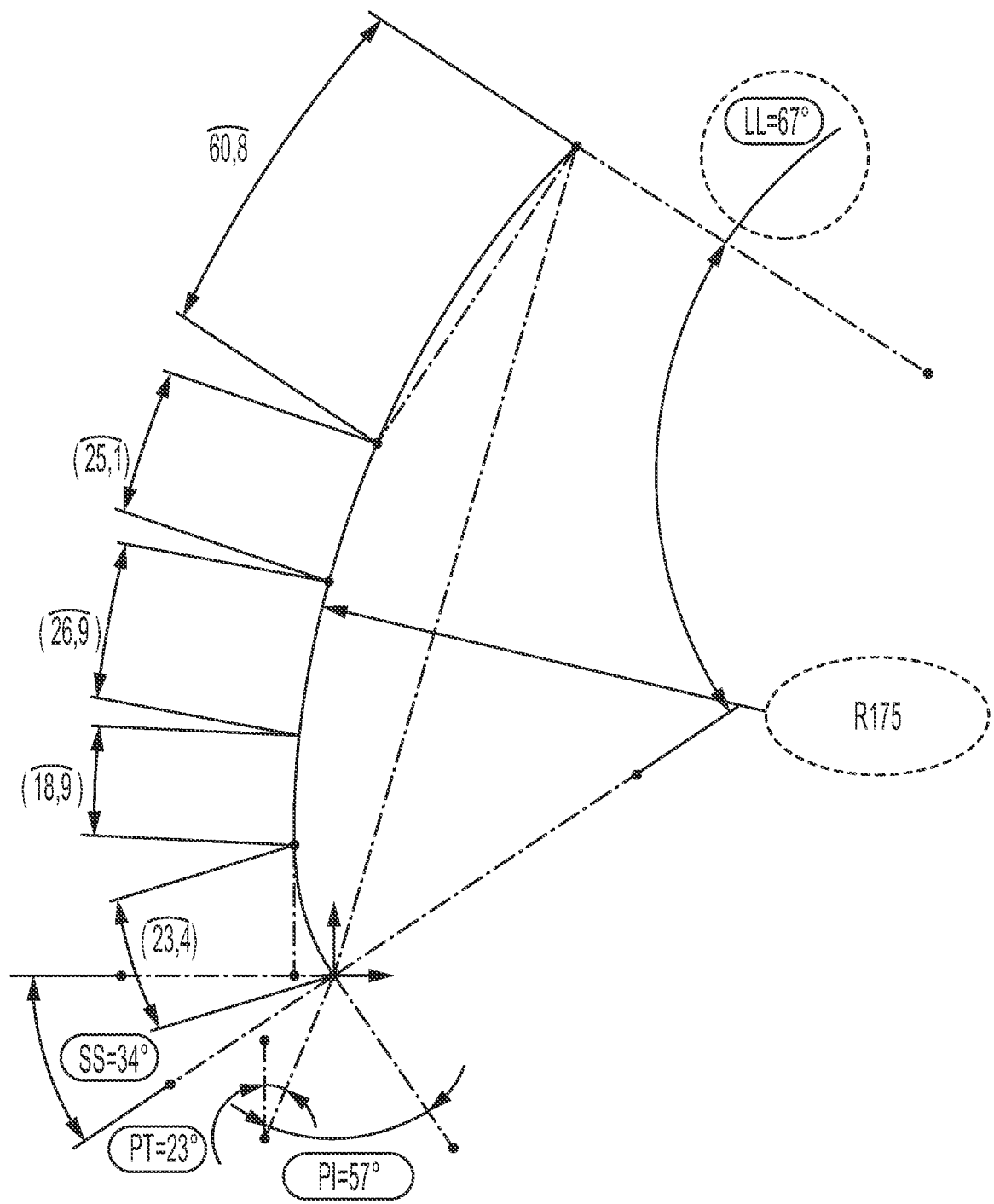

FIGS. 7 and 8: a wire model of the vertebral column of the patient is done, for example using CAD software;

FIG. 9: a reference centered at the plate of S1 is defined from said pelvic parameters, the origin point of that reference being the central point of that plate, then the different points of said cloud of points, attached to each vertebra, are positioned in that reference, and arcs between the identified points are drawn step by step, all of the arcs being tangent to each other and the arc extending from S1 being tangent to the straight line perpendicular to the plate of S1;

FIG. 10: the values of the arc lengths are read, and the correction to be applied to the lumbar segment to be treated is simulated as follows:
drawing a straight line tangent to the desired postoperative apex point, moving that straight line to a vertical position such that the arc attached to that straight line is tangent to that desired postoperative apex point, the latter thus being repositioned so as to become the apex point of the modeled vertebral column segment,
defining, as co-radial to each other, the arcs situated below that apex point and defining, as co-radial to each other, the arcs situated above that same apex point, so as to obtain two different curvatures, one above that apex point and the other below that apex point,
defining the lumbar lordosis as being equal to plus or minus ten degrees of the pelvic incidence, and defining, as desired, one of the three following values:
SVA distance smaller than 5 cm;
SVA/SFD ratio comprised between −1.9 and +0.1; the value of this ratio is positive on the side of the vertical V1 situated toward the femoral heads TF and is negative on the side of that vertical V1 situated opposite the femoral heads TF;
T1/SPI angle comprised between −9° and 0 0; this angle is negative on the side of the vertical V3 at the center of T1 located toward the femoral heads TF;
defining two arcs concentric to the two curvatures obtained in the above step, which are tangent to each other at the apex point, those arcs forming a curved segment SC representing the ideal curvature of the rod to be implanted in order to obtain the correction of the vertebral segment to be treated.

Figure 11:
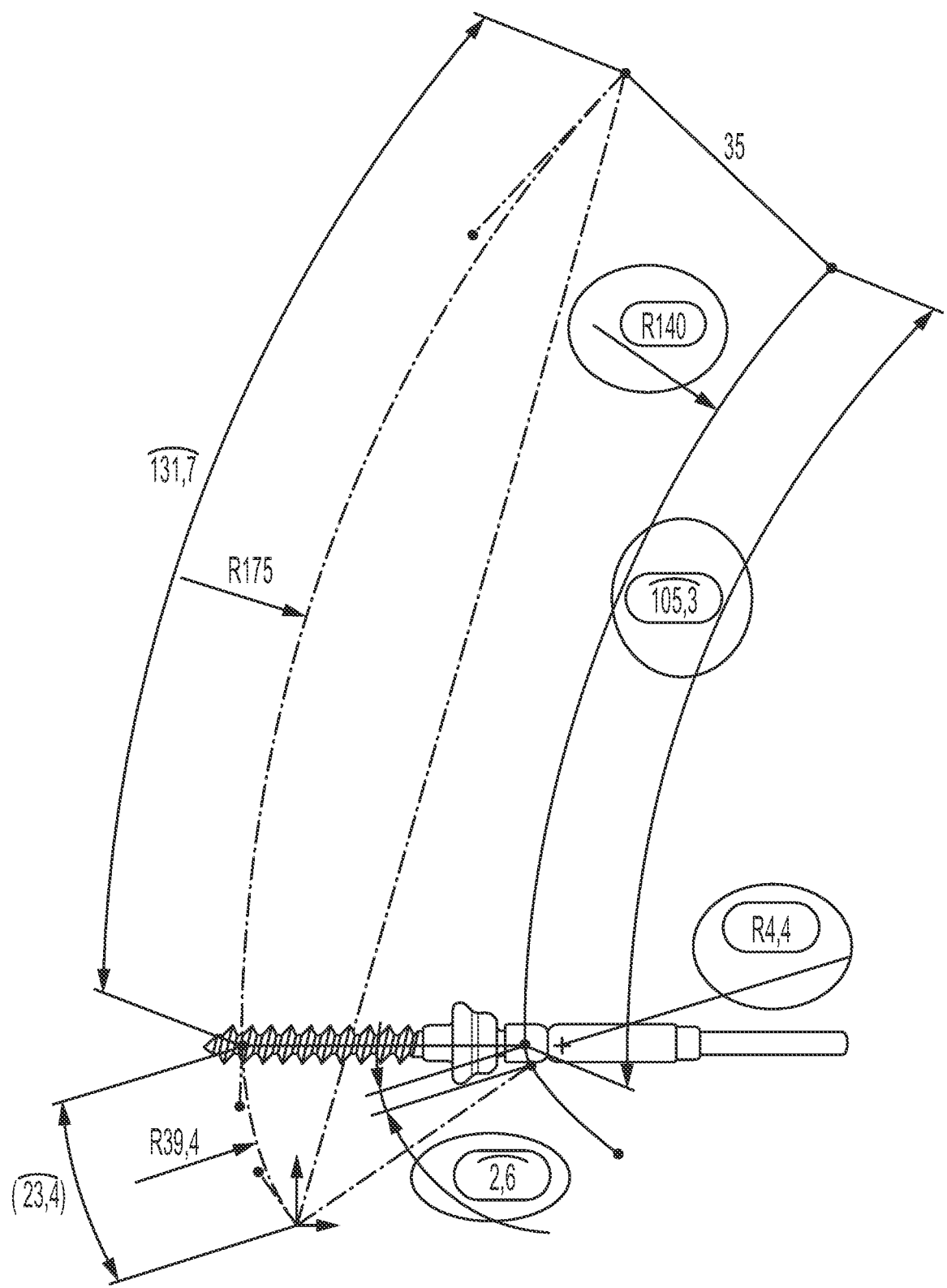

FIG. 11: the curved segment SC is translated away from the mean line of the vertebral column, over an evaluated mean distance going from the center of the vertebrae to the anchoring points of the anchoring members OA (FIG. 10, it is a pedicle screw) for anchoring the rod to the vertebrae of said vertebral segment to be treated, such that the position of said curve segment SC corresponds to the position that the rod will assume once implanted; the diameter of the rod to be implanted being defined, a two- or three-dimensional model of that rod is then established, curved along said arcs.

Figure 12:
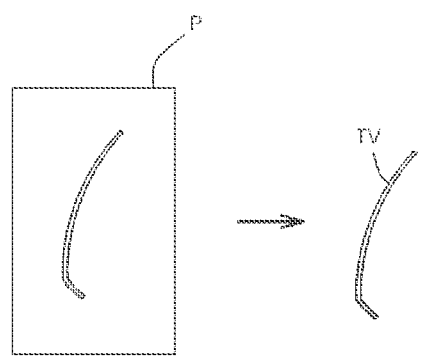
FIG. 12 is, on the left side of that figure, a view of a drawing or plan P of the curved vertebral rod to be obtained, the shape of which has been defined by the preceding steps of the method and, on the right side of that figure, a view of the curved vertebral rod TV, obtained from that drawing P.

FIG. 12: a drawing or plan P is established from that model, then the vertebral rod TV to be obtained is arranged from that drawing P, in particular by cold bending.

The method according to the invention thus has the decisive advantage of making it possible to produce the ideal curvature of a rod for vertebral osteosynthesis material designed to support a patient's vertebral column.

What is claimed is:

1. A method for producing a curvature of a rod of vertebral osteosynthesis material designed to support a vertebral column of a patient, the method comprising:
receiving, by a production unit, a model defining the curvature of the rod, the curvature of the rod being based on a pre-operative X-ray of the vertical column with a lumbar segment and representative of:
a simulated correction to be applied to the lumbar segment to be treated, wherein simulated correction comprises:
a repositioned postoperative apex point and a first curvature obtained above the repositioned apex point and a second curvature obtained below the repositioned apex point, and
data representative of a redefined lumbar lordosis;
a deduced curved segment representing the curvature of the rod based at least in part on one or more of the defined lumbar lordosis or the first curvature above the repositioned apex point and the second curvature below the repositioned apex point, and a translated curved segment representative of the deduced curve segment being translated away from a mean line of the vertebral column; and producing the rod by the production unit using computer aided design.

2. The method of claim 1, further comprising:
receiving a diameter of the rod.

3. The method of claim 1, wherein the curved segment represents a desired curvature of the rod to be implanted in order to obtain the correction of the lumbar segment to be treated.

4. The method of claim 1, wherein the correction is determined based on at least one measurement in the pre-operative X-ray, the at least one measurement comprises:
a SVA distance from a vertical of a posterior upper point of a plate of a first vertebra of a sacrum (S1) to a vertical passing through a center of a seventh cervical vertebra;
a SFD distance from the vertical of the posterior upper point of the plate of S1 to a vertical passing through a center of a femoral head; or
a T1/SPI angle formed between a segment going from a center of a first dorsal vertebra (T1) to the center of the femoral head and a vertical line extending from the center of T1.

5. The method of claim 4, wherein the at least one measurement is at least one redefined measurement, the at least one redefined measurement comprises:
a SVA distance smaller than 5 cm;
a SVA/SFD ratio comprised between −1.9 and +0.1 wherein the ratio is positive on the side of the vertical of the posterior upper point of the plate of S1 situated toward the femoral heads and is negative on the side of the vertical situated opposite the femoral heads; or
a T1/SPI angle comprised between −9° and 0°, that angle being negative on the side of the vertical at the center of T1 located toward the femoral heads.

6. The method of claim 1, wherein the postoperative apex point is defined by a vertebral column morphotype comprising one or more of:
a type 1 morphotype, in which a forwardmost point of the vertebral column is situated at a median plane of L5, and a sacral slope (SS) criterion corresponds to an angle smaller than 35';
a type 2 morphotype, in which the forwardmost point of the vertebral column is situated at a base of L4, and the SS criterion corresponds to an angle smaller than 35';
a type 3 morphotype, in which the forwardmost point of the vertebral column is situated at a median plane of L4, and the SS criterion corresponds to an angle between 35° and 45°; or
a type 4 morphotype, in which the forwardmost point of the vertebral column is situated at a base of L3, and the SS criterion corresponds to an angle larger than 45°.

7. The method of claim 1, wherein the producing includes producing the curvature of the by cold bending.

8. The method of claim 1, wherein:
the vertebral column extends from a cervical vertebrae to a femoral head a simulated correction; and
the curvature of the rod also being representative of two arcs concentric to the first and second curvatures obtained, which are tangent to each other at the apex point.

9. The method of claim 1, wherein the model is based on a defined vertebrae in which an anchor member for the rod to be anchored to the vertebrae will be implanted.

10. The method of claim 1, wherein the data representative of the redefine lumbar lordosis is equal to plus or minus ten degrees of a pelvic incidence, the pelvic incidence being represented in the pre-operative X-ray as an angle formed by a straight segment connecting a center of a femoral heads and a center of a plate of sacrum (S1) with the perpendicular to the plate of S1.

11. A system for producing a curvature of a rod of vertebral osteosynthesis material designed to support a vertebral column of a patient, the system comprising:
a production unit configured to receive data representative of a model defining the curvature of the rod and produce the rod using computer aided design, the curvature of the rod being based on a pre-operative X-ray of the vertical column with a lumbar segment and the model being representative of:
a simulated correction to be applied to the lumbar segment to be treated, wherein simulated correction comprises:
a repositioned postoperative apex point and a first curvature obtained above the repositioned apex point and a second curvature obtained below the repositioned apex point, and
data representative of lumbar lordosis;
a deduced curved segment representing the curvature of the rod based at least in part on one or more of the defined lumbar lordosis or the first curvature above the repositioned apex point and the second curvature below the repositioned apex point, and
a translated curved segment representative of the deduced curve segment being translated away from a mean line of the vertebral column,
the production unit configured to produce the rod by:
defining a diameter of the rod to be implanted based on the received model;
defining a three-dimensional plan of the rod based on the received model; and
using a straight rod having the defined diameter, cold bending the straight rod according to the defined three-dimensional plan.

12. The system of claim 11, wherein the curved segment represents a desired curvature of the rod to be implanted in order to obtain the correction of the lumbar segment to be treated.

13. The system of claim 11, wherein the correction is determined based on at least one measurement in the pre-operative X-ray, the at least one measurement comprises:
a SVA distance from a vertical of a posterior upper point of a plate of a first vertebra of a sacrum (S1) to a vertical passing through a center of a seventh cervical vertebra;
a SFD distance from the vertical of the posterior upper point of the plate of S1 to a vertical passing through a center of a femoral head; or
a T1/SPI angle formed between a segment going from a center of a first dorsal vertebra (T1) to the center of the femoral head and a vertical line extending from the center of T1.

14. The system of claim 13, wherein the at least one measurement is at least one redefined measurement, the at least one redefined measurement comprises:
a SVA distance smaller than 5 cm;
a SVA/SFD ratio comprised between −1.9 and +0.1 wherein the ratio is positive on the side of the vertical of the posterior upper point of the plate of S1 situated toward the femoral heads and is negative on the side of the vertical situated opposite the femoral heads; or a T1/SPI angle comprised between −9° and 0°, that angle being negative on the side of the vertical at the center of T1 located toward the femoral heads.

15. The system of claim 11, wherein the postoperative apex point is defined by a vertebral column morphotype comprising one or more of:
 a type 1 morphotype, in which a forwardmost point of the vertebral column is situated at a median plane of L5, and a sacral slope (SS) criterion corresponds to an angle smaller than 35';
 a type 2 morphotype, in which the forwardmost point of the vertebral column is situated at a base of L4, and the SS criterion corresponds to an angle smaller than 35°;
 a type 3 morphotype, in which the forwardmost point of the vertebral column is situated at a median plane of L4, and the SS criterion corresponds to an angle between 35° and 45°; or
 a type 4 morphotype, in which the forwardmost point of the vertebral column is situated at a base of L3, and the SS criterion corresponds to an angle larger than 45°.

16. The system of claim 11, wherein the vertebral column extends from a cervical vertebrae to a femoral head.

17. The system of claim 11, wherein the model is based on a defined vertebrae in which an anchor member for the rod to be anchored to the vertebrae will be implanted.

18. The system of claim 11, wherein the redefine lumbar lordosis is equal to plus or minus ten degrees of a pelvic incidence, the pelvic incidence being represented in the pre-operative X-ray as an angle formed by a straight segment connecting a center of a femoral heads and a center of a plate of sacrum (S1) with the perpendicular to the plate of S1.

* * * * *